United States Patent [19]
Taylor-McCord

[11] Patent Number: 5,266,318
[45] Date of Patent: Nov. 30, 1993

[54] SKIN THERAPEUTIC MIXTURE CONTAINING COLD-PROCESSSED ALOE VERA EXTRACT, WITH YELLOW SAP AND ALOIN REMOVED

[75] Inventor: Darlene Taylor-McCord, Dana Point, Calif.

[73] Assignee: Royale Renaissance, Inc., Dana Point, Calif.

[21] Appl. No.: 803,508

[22] Filed: Dec. 9, 1991

[51] Int. Cl.$^5$ .............. A61K 35/78; A61K 6/00; A61K 31/715; A61K 31/415

[52] U.S. Cl. ................. 424/195.1; 424/401; 514/54; 514/400; 514/552

[58] Field of Search .............. 424/195.1, 401; 514/552, 54, 400

[56] References Cited

U.S. PATENT DOCUMENTS

| | | | |
|---|---|---|---|
| 4,369,180 | 1/1983 | Mihalovits | 514/21 |
| 5,002,760 | 3/1991 | Katzev | 424/59 |
| 5,122,418 | 6/1992 | Nakane et al. | 424/401 |

*Primary Examiner*—John W. Rollins
*Attorney, Agent, or Firm*—Daniel L. Dawes

[57] ABSTRACT

According to present invention, a non-ionic skin therapeutic mixture useful for treatment of irradiated skin, open sores, wounds and abrasions is comprised of an extract of cold-processed aloe vera gel, with yellow sap and aloin removed to ensure the bradykininase activity has been preserved during the extracting process. The mixture includes in combination allantoin and lavender essential oil to form a unique and synergistic product for enhanced healing with treatment of swelling. Additionally, an effective amount of an acceptable topical carrier or a cosmetically acceptable surfactant, and a cosmetically acceptable preservative is included. The compositions of the invention may be in the form of a liquid, creme, ointment, paste, gel or powder.

21 Claims, No Drawings

SKIN THERAPEUTIC MIXTURE CONTAINING COLD-PROCESSSED ALOE VERA EXTRACT, WITH YELLOW SAP AND ALOIN REMOVED

BACKGROUND OF THE INVENTION

1. Field of the Invention

This invention relates to topical formulations for treatment of damaged skin, such as irradiated skin in combination with wound treatment. In particular, the invention relates to topical formulations useful for the treatment of skin damaged by the harmful effects of radiation and radioactive substances, such as used in the treatment of cancer or exposure to the sun, open sores, wounds and abrasions.

2. Description of the Prior Art

According to the American Cancer Society's Cancer Facts and FIGS.-1991, at the current rate, about 76 million Americans now living will eventually have cancer. It will strike three of four families. Cancer strikes at any age. It kills more children of age 1 to 14 in the United States than any other disease and occurs more frequently with age. Based on current medical technology over half of these cancer patients will undergo some form of radiation therapy.

In the 1930's, less than one in five was alive at least five years after treatment. In the 1940's, it was one in four, and in the 1960's, it was one in three. Today about 440,000 Americans, or 4 of 10 patients who get cancer, will be alive five years after diagnosis. The gain from 1 in 3 to 4 in 10 represents about 77,000 persons this year.

The primary goal of the medical community has been to prolong the life of cancer patients. Until recently, and in relation to the growing number of cancer patients that can expect to survive five years or more, the quality of life of the cancer patient has received attention.

The onset of radiodermatitis as a result of irradiation in cancer patients is well documented. It is characterized by congestive or exudative redness of the skin caused by hyperthermia. Therefore, there is a need for substances effective for treating irradiated skin damage or radiodermatitis.

The topical use of anti-inflammatory agents to alleviate radiodermatitis is known. Such compositions contain combinations of one or more steroidal anti-inflammatories, non-steroidal anti-inflammatories, as well as "natural" anti-inflammatories, such as an extract of aloe vera.

The "greying of America" is also well documented. People are living longer and have expectations for a quality life as well as a long life. People afflicted with long term illness run the risk of getting bed sores, pressure sores and a myriad of skin irritations due to incontinence.

Looking at the treatment figures for pressure ulcers, just a small part of the entire market, one can quickly see that there is a need to develop products that will effectively treat patients with long term illnesses.

As part of a study using AMA data on admissions to acute hospitals to derive the number of patients at risk of pressure ulcers, the statistics and forecasts are as follows:

TABLE 1

| Pressure Ucleration in U.S. Hospitals PATIENTS (1000's) | | | | | |
|---|---|---|---|---|---|
| | 1989 | 1990 | 1995 | 2000 | 2005 |
| STAGE 1 | 539 | 547 | 596 | 656 | 718 |
| STAGE 2 | 779 | 790 | 861 | 947 | 1037 |
| STAGE 3 | 180 | 182 | 199 | 219 | 239 |
| STAGE 4 | 180 | 182 | 199 | 219 | 239 |
| TOTAL | 1677 | 1701 | 1853 | 2040 | 2233 |

Therefore, there is a need for a substance which will reduce bed sores or ulceration.

The bradykininase activity or ability to reduce swelling which is present in cold-processed aloe vera, with yellow sap and aloin removed, is clinically proven when used in high concentrations. See, K. Fujita, R. Teradair, and T. Nagatsu, Biochem. Pharm., Vol. 25, 205, 1976.

However, some extracts of aloe vera have been found to be toxic and the applicability of aloe vera for treatment of skin disorders is not generally accepted or understood. Winters et al. conducted a study to determine the toxicity of yellow sap and aloin on human skin cells (fibroblast) that were obtained from human foreskin. The cells were grown in MEM supplemented with 5 percent human serum. The yellow sap was tested at 1, 10, 15, and 30 percent and compared to untreated control cells. There was a 100 percent cell kill recorded at all levels when yellow sap was applied to fibroblast. I. Danhof, Ph.D., M.D. and B. McAnalley, Ph.D., "Stabilized aloe vera: Effect on human skin cells", D&CI, 4-5, 105-106, (August 1983).

Several prior art patents disclose cosmetic/therapeutic formulations including aloe vera. DeNavarre, "Non-irritating Antiperspirant" U.S. Pat. No. 4,302,443 discloses the use of aloe vera to prevent irritation. DeNavarre does not claim to use fresh aloe vera that has been filleted with the outer rind, yellow sap and aloin removed by a cold-process to produce a substantially anthraquinone-free fillet that is ground, homogenized and processed into a stable aloe vera extract. There is also no combination in DeNavarre with allantoin and lavender essential oil, or any claim for the treatment of irradiated skin, open sores, wounds or abrasions.

Mihalovits, "Cosmetic Facial Preparation Containing Aloe Vera" U.S. Pat. No. 4,369,180 discloses the use of aloe vera in combination with cornstarch or cosmetic clay, albumin, allantoin, vitamin A, vitamin D2, and vitamin E. Mihalovits also does not claim to use fresh aloe vera that has been filleted with the outer rind, yellow sap and aloin removed by a cold-process to produce a substantially anthraquinone-free fillet that is then ground, homogenized and processed into a stable aloe vera extract. Mihalovits teaches the use of allantoin, but only in formulations at 0.5% by weight, which is significantly less than the present invention, and makes no claims for the use of lavender essential oil. Mihalovits further makes no claims as a treatment for irradiated skin, open sores, wounds or abrasions.

Millard, "Skin Treatment Preparation" U.S. Pat. No. 4,505,902 discloses a formulation which uses aloe vera juice in combination with mineral oil, apricot kernel oil, avocado oil, and cod liver oil. Millard does not claim to use fresh aloe vera that has been filleted with the outer rind, yellow sap and aloin removed by a cold-process to produce a substantially anthraquinone-free fillet that is then ground, homogenized and processed into a stable aloe vera extract. There is no teaching to combine it with allantoin and lavender essential oil, and no claims as a treatment for irradiated skin, open sores, wounds or abrasions.

Trenzeluk, "*Skin Therapeutic Mixture Containing Aloe Vera Extract*" U.S. Pat. No. 4,857,328 discloses a formulation using the dried leaves of the aloe vera plant as the therapeutic agent for the treatment of acne, psoriasis, burns, pimples, blackheads, and open sores. Trenzeluk directs the use of dried leaves of the aloe vera plant and does not claim to use fresh aloe vera that has been filleted with the outer rind, yellow sap and aloin removed by a cold-process to produce a substantially anthraquinone-free fillet that is then ground, homogenized and processed into a stable aloe vera extract. There is not teaching relating to the combination with allantoin and lavender essential oil.

Therefore, it is an object of the present invention to provide a phase stable topical formulation, which uses the extract from cold-processed aloe vera gel, with yellow sap and aloin removed, combined with allantoin and lavender essential oil, the use of which will provide treatment of radiodermatitis and the chronic effects of radiation exposure without interfering with the radiation therapy, treatment of open sores, wounds or abrasions.

It is also an object of the present invention to provide a phase stable cleansing composition, which uses the extract from cold-processed aloe vera gel, with yellow sap and aloin removed, combined with allantoin and lavender essential oil, the use of which will provide a method for relieving the deleterious effects of radiation without interfering with the radiation therapy, treatment of open sores, wounds or abrasions.

BRIEF SUMMARY OF THE INVENTION

The present invention is a class of formulations containing a high level of cold-processed aloe vera extract, with yellow sap and aloin removed, combined with allantoin and lavender essential oil, and a topical carrier to create a unique therapy for the management of open sores, wounds and abrasions. The anti-inflammatory action of aloe vera, used in combination with allantoin and lavender essential oil, has a unique synergistic effect that is effective in the treatment of open sores, wounds and abrasions. This healing effect of the mixture exceeds that which is known for allantoin alone to help heal wounds and skin ulcers and to stimulate the growth of healthy tissue.

The present invention also relates to formulations useful for treating the radiodermatitis caused by irradiation on skin comprising the extract from cold-processed aloe vera gel, with yellow sap and aloin removed, combined with allantoin and lavender essential oil, and a safe and effective amount of a topical carrier.

The present invention also relates to formulations useful in treating open sores, wounds or abrasions on skin comprising the extract from cold-processed aloe vera gel, with yellow sap and aloin removed, combined with allantoin and lavender essential oil, and a safe and effective amount of a topical carrier.

More specifically the invention is a mixture for treatment of irradiated skin, open sores, wounds and abrasions. The mixture comprises a substantially anthraquinone-free cold processed fresh aloe vera extract. The aloe vera extract comprises from about 1 percent by weight per unit volume up to about 98 percent per unit volume. Allantoin comprises from about 0.10 percent by weight per unit volume up to about 8 percent by weight per unit volume. As a result, a combination is provided which synergistically increases the healing effect of each the mixture over that provided separately by its constituents.

The mixture further comprises a topical carrier. The mixture still further comprises a nondegradable extract of lavender essential oil from about 0.01 percent by weight per unit volume up to about 2 percent by weight per unit volume.

The mixture may include a cosmetic surfactant and a cosmetic preservative.

In one embodiment the aloe vera extract comprises from about 40 percent by weight per unit volume to about 95 percent by weight per unit volume. The allantoin comprises from about 1 percent by weight per unit volume to about 2 percent by weight per unit volume.

The fresh aloe vera has been processed from an aloe vera plant having an outer rind, sap and containing aloin. The outer rind, yellow sap and aloin are removed by a conventional cold process to produce the substantially anthraquinone-free aloe vera extract. The anthraquinone-free aloe vera extract is ground, homogenized and processed into a stable aloe vera extract.

In another embodiment the lavender essential oil comprises from about 0.03 percent by weight per unit volume up to about 0.09 percent by weight per unit volume.

Other ratios of the active ingredients are also contemplated in the invention. For example, the aloe vera extract may comprise about 77.7 percent by weight per unit volume and the allantoin comprises about 2 percent by weight per unit volume. Alternatively, the aloe vera extract comprises about 93.8 percent by weight per unit volume and the allantoin comprises about 2.0 percent by weight per unit volume. In yet another embodiment the aloe vera extract comprises about 45.2 percent by weight per unit volume and the allantoin comprises about 2.0 percent by weight per unit volume.

More generally the invention is a mixture for damaged skin comprising an element for reducing inflammation of the skin, and an element for simultaneously healing the skin. The element for reducing inflammation coacts with the element for healing the skin to accelerate the action of the element for healing. The mixture further comprises an element for calming nervous activity while simultaneously providing the element for reducing inflammation and element for healing to holistically coact with each other to heal.

The invention can better be understood by turning to the examples in the following detailed description.

DETAILED DESCRIPTION OF THE INVENTION

In accordance with the present invention, there is provided herein formulations useful for topical application comprising the extract from cold-processed aloe vera gel, with yellow sap and aloin removed, combined with allantoin and lavender essential oil, and a safe and effective amount of a topical carrier.

According to present invention, a non-ionic skin therapeutic mixture useful for treatment of irradiated skin, open sores, wounds and abrasions is comprised of an extract of cold-processed aloe vera gel, with yellow sap and aloin removed to ensure the bradykininase activity has been preserved during the extracting process. The mixture includes in combination allantoin and lavender essential oil to form a unique and synergistic product for enhanced healing with treatment of swelling. Additionally, an effective amount of an acceptable topical carrier or a cosmetically acceptable surfactant, and a cosmetically acceptable preservative is included. The compositions of the invention may be in the form of a liquid, creme, ointment, paste, gel or powder.

Extract of Aloe Vera Gel

Aloe is a tropical or subtropical plant that is a member of the lily family. There are about 325 species of Aloe known, and most are indigenous to Africa. Aloe barbadensis is a native of northern Africa, and was introduced into the island of Barbados in about 1630. Aloe barbadensis Miller has a short, woody stem, and lancelolate embracing leaves, of glaucous green color, with hard, pale spines. It is now grown commercially in the Rio Grande region of Texas.

The mucilaginous jelly from the parenchymal cells of the plant is referred to as aloe vera gel. There are generally no anthraquinones to decompose and cause discoloration of the gel unless the gel is contaminated by an improper processing technique. Aloe vera gel is about 98.5% water by weight. More than 60% of the total solid is made up of polysaccharides of carbohydrate origin. Organic acids and inorganic compounds, especially calcium oxalate, account for the remainder of the solid.

Whole leaves, exudates and fresh gels of aloe plants have been used for a variety of human afflictions. Evidence of their use as medicinal remedies can be traced to the Egyptians of 400 BC. Aloe vera has enjoyed a long history of lay acceptance as possessing "curative" or "healing" qualities. Over the last few years, numerous books and articles meeting scientific standards have been written on aloe vera. Aloe vera has been featured extensively in the field of dermatology, especially for treating radiation-caused skin conditions. See, Mackee, X-Rays and Radium in the Treatment of Diseases of the Skin, 3rd Ed., Lea and Febiger, Philadelphia, 319-320 (1938); Rovalti et al., Industrial Medicine and Surgery, 28: 364-368 (1959).

Presently, there has been controversy over the identity of the active substances in aloe vera. It is therefore important to clearly distinguish between the components of the present invention and those found in the exudates found in aloe vera that employs the use of the whole leaf without the aloin and yellow sap being removed.

The harvesting and extracting of aloe vera has been hindered by the lack of knowledge about the aloe plant and its characteristics. Methods currently employed for the processing of the plant and its components result in end products which do not consistently achieve desired results because of the presence of yellow sap, which is known to be cytotoxic to skin. For example, Cobble, U.S. Pat. No. 3,892,853 and Coats, U.S. Pat. No. 4,178,372 both teach a process for producing an alleged stabilized (i.e. bacteriologically stable) aloe juice by extracting the mucilage from the aloe leaves and adding a mild oxidant (H202). No reference is made to removing yellow sap.

These processes for example, typically involve crushing (pressure rollers), grinding (e.g., use of Thompson aloe leaf slitter), or pressing (TCX pressure extruder) the entire leaf of the aloe plant to produce an aloe vera juice, which is filtered and used in cosmetics and topical ointments. It can be appreciated that crushing the whole leaf of aloe vera and/or chemically altering the substance, without removing the yellow sap, instead of separating the constituents prior to processing, and insuring the removal of all yellow sap, alters the chemical composition of the aloe vera extract.

Winters' conclusion that "The cytotoxic effects of commercially prepared aloe vera gel fractions on normal human and tumor cells in culture", suggests that these commercial preparations contain substances introduced during commercial processing which can alter the levels of lectin-like activities and can markedly disrupt the in vitro attachment and growth of human cells". Winters et al. reported to the instant applicant that he used material received from Coates as a commercial stabilized aloe preparation.

Recent studies indicate that the yellow sap found just under the outer green waxy surface of the aloe vera plant is toxic to human skin cells. I. E. Danhof et al., "*Stabilized Aloe Vera: Effect on Human Skin Cells*", D & CI, 52-54, 105-106 (August, 1983). He reported the use of products with yellow sap should be minimized in topical products where it can come in contact with broken or damaged skin. Idiosyncratic hypersensitivity has been demonstrated in processed aloe vera gel that consists of a variable mixture of yellow sap. D. M. Morrow, M.D., et al, "*Hypersensitivity to Aloe*", ARCH. DERMATOL., 116, 1064-165 September 1980).

McAnalley, U.S. Pat. Nos. 4,966,892, 4,917,890 and 4,735,935 teach a process for producing an alleged stabilized aloe mucilaginous that is a "substantially" anthraquinone free extract. No reference is made to color stability or to the removal of aloin to <5 ppm. In fact, literature describing the aloe extract obtained using the McAnalley process addresses the inability of the extract to maintain color stability.

While the McAnalley process is an improvement over the Cobble and Coates methods, it still falls short of reasonable stability expectations and allows for challenge to the overall chemical stability of the product produced using the McAnalley process.

The invention is directed to use aloe vera that has been extracted in a manner that is chemically stable as well as color stable, that renders the chemical substance substantially non-degradable and can be administered in a prescribed amount. It has been cold-processed to retain all natural enzymatic activities and to preserve heat sensitive constituents. It is prepared from mature leaves, harvested at peak conditions. Aloin is removed by non-chemical means (<5 ppm in 1:1 aloe vera) to obviate leeching of natural ingredients. The aloe vera gel is treated with a unique double control system that guarantees microbiological stability. It is subjected to rigorous quality control procedures that assure enviable batch-to-batch consistency for a botanically derived product.

Allantoin

Allantoin has not suffered from the challenge to its effectiveness that aloe vera extract has had to endure. Allantoin is chemically a diureide of glyoxylic acid and thus is an urea derivative. Its use as a therapeutic agent in dermatology was based formerly on its ability to facilitate the removal of necrotic tissue and to stimulate wound healing by promoting cell proliferation. E. Young, "*Allantoin in Treatment of Psoriasis*", Dermatologica, 147: 338-341 (1973). It can be prepared synthetically by the oxidation of uric acid or by heating uric acid with dichloroacetic acid. Uric acid is prepared from urea and is present in the urine of all carnivorous animals.

Allantoin is an important ingredient which stimulates healing of wounds, and burns and which increases hydration and elasticity of skin. M. Sznitowska and S Janicki, "*The Effect of Vehicle on Allantoin Penetration into Human Skin from an Ointment for Improving Scar Elasticity*", Department of Pharmaceutical Technology, Medical Academy, Gdanks, Poland (October 1987).

The FDA-OTC Topical Analgesic Review Panel recently classified allantoin in Category I (Safe and Effective) as an active skin "protectant." The FDA monograph on skin protectant published in the Federal Register (Vol.43 No. 151) on Aug. 4, 1978, stated that, based on the wide use and clinical acceptance of allantoin, as well as on published reports in the literature, the Panel approved the following statements for products containing allantoin:

"Temporarily relieves, protects, soothes, gives comfort to minor skin irritations, such as chapping, peeling, scaling, minor burns, sunburn, windburn, scrapes, abrasions or cracked lips."

While the attributes of allantoin have been clinically proven and the FDA has classified it in Category I (Safe and Effective), there remain difficulties in the manufacturing process as related to allantoin with a mesh size of 200 or less.

Allantoin is water soluble to 0.50%, according to A. Fisher, M.D., "*Allantoin: A Non-sensitizing Topical Medicament: Therapeutic Effects of the Addition of 5.00% Allantoin to Vaseline*", Currnet Contact News, vol. 27, 230–231, 234–235, (March 1981).

The industry standard 200 mesh particle size, when used in higher by-weight percentages (over 0.50%), tends to crystalize and fall-out. Fall-out reduces the effectiveness of the mixture and crystallization alters the texture.

In order to overcome fall-out and crystallization the present invention is directed to use 400 mesh allantoin or finer. A unique process micronizes the allantoin in a manner that allows for the reduction of particle size by 50%. Four hundred mesh allantoin provides for improved product shelf-life, reduced crystallization, and greater absorption of the ingredient into the mixture.

Extract of Lavender

Lavender is a shrubby plant indigenous to the mountainous regions of the countries bordering the western half of the Mediterranean, and cultivated extensively for its aromatic flowers in various parts of France, Italy and England. There are four major varieties of lavender. One is spike lavender (Lavandula Latifolia). This is a strong growing shrub that grows naturally at lower altitudes around the northern Mediterranean shore, particularly Spain and Italy. A second is true lavender (*Lavandula angustifolia*). This is a dwarf shrub that is distinguished from all others by being camphor free. Its natural habitat is restricted to a small area above 1000 meters altitude in the southern French Alps. A third is lavandin (Hybrid: L. Latifolia XL. angustifolia). This is grown as a natural hybrid at medium altitudes in the south of France. It has a high camphor content.

Finally, there is *Lavendula officinalis*. This is the true lavender which grows wild at altitudes of 700–1100 meters in southern France. The preferred embodiment of the invention directs the use of extracts derived from the flowers and leave from the Lavendula officinalis.

The Greeks called lavender by the name Nardus, from Naarda, a city of Syria near the Euphrates. St. Mark mentions it as Spikenard, a thing of great value . .. In Pliny's time, blossoms of the nardus, called asarum by the Romans, sold for a hundred Roman denarii. The Romans use of lavender is well documented. Lavender is also cited as one of the ingredients of the 'Four Thieves' vinegar famous in the Middle Ages.

The use of lavender in the present invention employs the belief that a patient must be treated holistically. Bach et al., stated 'the second duty of the physician will be to administer such remedies as will help the physical body to gain strength and assist the mind to become calm'.

Essences work organically and can replace the use of tranquilizers. There use dates back to antiquity when such physicians as Galen and Celsus used aromatic herbs as remedies against hysterical convulsions, and reported that they sometimes stopped attacks immediately Unlike the modern sleeping pill, essences are not mere sedatives. Most of them are very pleasant to smell providing the uplifting effect, a more positive attribute than for that of a sedative. R. Tisserand, "*The Art of Aromatherapy*", Destiny Books, 95–101, (1977).

Mme Maury et al. stated, 'but of the greatest interest is the effect of the fragrance on the psychic and mental state of the individual. Powers of perception become clearer and more acute, and there is a feeling of having to a certain extent, outstripped events. They are seen more objectively and therefore in truer perspective. Ift might even be said the emotional trouble which in general obscures our perception is practically suppressed'.

Professor Rovesti has studied the effects of essences on the human psyche and states:

"According to sociologists and neurologists the salient characteristics of our age are those of anxiety and depression, and material proof of this is available in the even higher figures shown for the consumption of tranquilizers and stimulants. It is well known that disturbance and toxicosis can be caused by these products if taken regularly."

"Both neuroses often causes aversion to any type of pleasure, by producing a sense of weariness which many people are unable to overcome."

"The possibility of applying new therapies to these widespread psycho-neuroses is therefore of considerable importance."

"For such purposes, therefore, interest attaches to the use of essential oils as aids, or even as sole remedies in psychotherapy."

"The matter is of still further interest, since the essential oils that are employed in aromatherapy, in the appropriate doses, are harmless to the organism and do not cause troubles like those produced by the ordinary psychological drugs. Very conclusive experiments in this direction have been carried out in various clinics for nervous diseases, on patients affected by hysteria or psychic depression."

Lavender is listed as an effective means to improve the physical condition of patients in two areas. It is mentioned in the treatment of anxiety and nervous tension, and for depression and melancholy. R. Tisserand, "The art of aromatherapy", Destiny Books, 95–101, (1977).

The trust of lavender is still widely held in Europe. Some of this trust is founded upon the use of lavender during World War I to swab the wounds of soldiers. The French Academy of Medicine is giving attention to the oil of lavender for this and other antiseptic surgical purposes. The oil is successfully used in the treatment of sores, varicose ulcers, burns and scalds. Peter Smith, et al,; and Grieve, A Modern Herbal, vol. 2, 467–473 (1981).

French chemist Rene-Maurice Gattefosse found early in this century, an essential-oil house that produced oil for use in cosmetics and fragrances. It is alleged one day Gattefosse burned his hand in his laboratory. Remembering that lavender was supposed to heal burns and reduce inflammation, he immediately immersed his hand in a container of pure lavender on his workbench. The burn quickly lost its redness, and began to heal.

French lavender is rich in folklore. It has been endowed with many rich qualities. Used externally, it is believed to be antiseptic and disinfectant. It is believed to be helpful in healing wounds, sore and skin ulcers.

The harvesting of lavender takes great care. The stalks of lavender are spread out in the open, on trays or sieves, in a cool, shady place, out of the sun, so that they may dry slowly. The trays are raised a few feet from the ground, to ensure a warm current of air, and the stems are not allowed to touch, or the flowers will be spoiled by the moist heat engendered. Lavender is taken indoors before there is any risk of getting damp either by dew or showers. When dry, it is stored in a dry place and the flowers stripped from the stalks and dried by a moderate heat.

The current invention is directed to use lavender that has been extracted in a manner that renders the chemical substance substantially non-degradable and can be administered in a prescribed amount. It has been cold-processed to retain all natural activities and to preserve heat sensitive constituents. It is prepared from flowers and leaves of mature plants, harvested at peak conditions. The lavender is subjected to rigorous quality control procedures that assure enviable batch-to-batch consistency for a botanically derived product.

Topical Compositions

In addition to the active agents of extract of cold-processed aloe vera, with yellow sap and aloin removed, combined with allantoin and lavender essential oil, the compositions of the present invention contains a safe and effective amount of an acceptable topical carrier. The term "acceptable topical carrier" encompasses both pharmaceutically-acceptable carriers and cosmetically-acceptable carriers, and encompasses substantially non-irritating compatible components (either taken alone or in mixtures) which are suitable for delivering the active components to the skin. The term "compatible", as used herein, means that the components of the carrier must be capable of being commingled with cold-processed aloe vera extract, with yellow sap and aloin removed, combined with allantoin and lavender essential oil, in a manner such that there is no interaction which would substantially reduce the efficacy of the composition during use for protecting the skin from the effects of radiation and in the treatment of open sores, wounds or abrasions. These carriers must, of course, be of sufficiently high purity and sufficiently low toxicity to render them suitable for chronic topical administration to the skin of humans or lower animals. The term "safe and effective amount" of carrier means an amount sufficient to deliver the aloe vera extract to the skin but not so much as to cause any side effects or skin reactions.

The topical compositions of the present invention contain generally from about 1% to 98% by weight preferably from about 40% to 95% by weight cold-processed aloe vera extract, with yellow sap and aloin removed, combined with 0.10% to 85 by weight preferably from 1% to 2% by weight allantoin, and combined with from 0.01% to 2% by weight preferably from 0.03 to 0.09% by weight levender essential oil.

Variations in formulation of these carriers will result in a wide variety of products which fall within the scope of the present invention. These product types can be divided into two classes: pharmaceutical/cosmetic compositions and cleaning compositions.

Pharmaceutical/Cosmetic Compositions

The invention relates to mixtures containing cold-processed aloe vera extract with yellow sap and aloin removed in combination with allantoin and levender essential oil. The pharmaceutical/cosmetic compositions of the present invention may be made into a wide variety of product types. These include, for example, lotions, creams, gels, sprays, ointments, rinses, toothpaste and powders.

It has been said, "We know more about traveling into space than how the body repairs itself". At birth, a baby's body knows more about the healing process than the combined knowledge of man. An injury to the soft tissues of the body starts a complicated chain of events that have outward manifestations including, redness, heat, swelling, pain and tissue death due to the loss of oxygen to the area. These events take place within minutes of an injury. One of the body's fundamental reactions to injury is acute inflammation. It is the body's way to protect, localize and rid the body of injurious agents in preparation for healing and repair. Inflammation is a natural way in which pain is used to cause a change in the behavior of the animal to avoid reinjury of the affect site until healing is completed.

It is important to note the two distinct bodily activities. First, the body responds with inflammation as a way to protect itself and rid itself of injurious agents. Secondly, the body starts the healing and repair phase.

A key event that takes place in the "first stage" of soft tissue trauma is a chemical response called bradykinin which results in the creation of pain. This is the release of a peptide (bradykin), which is a fragment of a large protein molecule that circulates in the blood stream. When tissue is damaged in any way, tiny capillaries break, releasing bradykin into the affected area. The release of bradykin also triggers a chemical reaction know to be responsible for sending the pain message to the brain.

During the bradykinin response cellular death occurs, due to the loss of oxygen to the cells, caused in part by inflammation. If cell loss is to be minimized, it is important to as quickly as possible reverse the bradykinin response, the very response the body has engineered to protect itself.

Cold-processed aloe vera extract, with yellow sap and aloin removed, is clinically proven to have a bradykininase effect on human tissue (fibroblast). Bradykininase activity simply means to slow or stop the release of bradykin. This important "first step", the application of properly processed aloe vera extract, helps calm the affected area and allows for an orderly commencement of the healing process. K. Fujita, R. Teradaira, and T. Nagatsu, "*Bradyininase Activity of Aloe Extract*", Biochem. Pharm., 205, (August 1975).

Tissue repair or regeneration takes place during the healing process. There are three ways in which the tissue can heal: (1) normal restoration; (2) formation of granulation tissue (if restoration is delayed); and (3) regeneration, the replacement of tissue by the same tissue. Van der Meulen et al., commented, "In man—unlike the salamander, which can regrow an amputated limb—the capacity for regeneration is limited to a few cells, which comprise the endothelial cells, the fibroblasts and the epithelial cells."

The ability for cells to regenerate deteriorates with age. As people live longer it is important to find ways to assist in the healing and regeneration process. Allantoin, a derivative of uric acid, is clinically proven to be a cell proliferator. In other words, cells multiply more quickly in the presence of allantoin than without. M. Szniroqak, and A. Janicki, Pharmazie, 45, 218, (1988).

Just as the body demonstrates a coordinated inflammation-healing process, the present invention produces a synergy by combining the appropriate aloe vera extract with allantoin to initiate a process to reduce inflammation-promote healing. The aloe vera reduces inflammation to keep oxygen levels in the cell environment from being reduced. This has the synergistic effect that the aloe vera then allows the allantoin to work more effectively with the surviving cells in a more oxygen rich environment.

The present invention is holistic in its approach to healing with the addition of lavender essential oil, which has been proven to reverse the effects of anxiety and nervous tension characteristically found in patients undergoing treatment. Lavender is additive to the aloe vera extract and allantoin, in that it brings peace of mind, aromatherapy, into play while the body works to heal itself. R. Tisserand, "*The Art of Aromatherapy*", Destiny Books, 95–101, (1977).

Cleaning Compositions

The skin/hair cleaning compositions of the present invention comprise, in addition to aloe vera extract, allantoin and lavender essential oil, a cosmetically-acceptable surfactant. The term "cosmetically-acceptable surfactant" refers to a surfactant which is not only an effective skin/hair cleanser, but also can be used without undue toxicity, irritation, allergic response, and the like. Furthermore, the surfactant must be capable of being commingled with cold-processed aloe vera extract, with yellow sap and aloin removed, combined with allantoin and lavender essential oil, in a manner such that there is no interaction which would substantially reduce the efficacy of the composition for protecting the skin/hair.

The skin/hair cleansing compositions of the present invention contain from about 1% to 98% by weight, preferably 40% to 95% by weight cold-processed aloe vera extract, with yellow sap and aloin removed, combined with 0.10% to 8% by weight preferably 1% to 2% by weight allantoin, and combined with 0.01 to 2% by weight preferably from 0.03% to 0.09% by weight lavender essential oil.

The cleaning compositions of the present invention may be made into a wide variety of product types. These include, for example, body lathers, facial lathers, shampoos, and toilet bars.

EXAMPLE I

A therapeutic skin lotion is prepared by combining the following components utilizing conventional mixing techniques.

TABLE 2

Therapeutic Skin Lotion

| INGREDIENT | PERCENTAGE BY WEIGHT |
| --- | --- |
| Aloe Vera Extract | 77.70% |
| Allantoin | 2.00% |
| Walnut Oil | 2.00% |
| Tocopherol Acetate (Vitamin) | 2.00% |
| Stearic Acid | 2.00% |
| 1-Hexadecanol | 2.00% |
| Polysorbate-60 | 2.00% |
| Apricot Kernel Oil | 2.00% |
| Jojoba Oil | 2.00% |
| Glyceryl Stearate | 2.00% |
| PEG-100 Stearate | 1.00% |
| Dimethicone | 1.00% |
| Whole Wheat Protein | 1.00% |
| Triethanolamine | 0.60% |
| Carbomer-940 | 0.20% |
| Methylparaben | 0.20% |
| Quanternium-15 | 0.15% |
| Propylparaben | 0.10% |
| Lavender Essential Oil | 0.05% |

EXAMPLE II

A therapeutic skin gel is prepared by combining the following components utilizing conventional mixing techniques.

TABLE 3

Therapeutic Skin Gel

| INGREDIENTS | PERCENTAGE BY WEIGHT |
| --- | --- |
| Aloe vera extract | 93.80% |
| Allantoin | 2.00% |
| Tocopherol Acetate (vitamin) | 2.00% |
| Triethanomine 85% | 1.00% |
| Carbomer-940 | .50% |
| Panthenol | .20% |
| Sodium PCA | .20% |
| Potassium Sorbate | .10% |
| Sodium Citrate | .10% |
| Tocopherol | .05% |
| Lavender Essential Oil | .05% |

EXAMPLE III

A therapeutic body cleansing lather is prepared by combining the following components utilizing conventional mixing techniques.

TABLE 4

Therapeutic Body Cleansing Lather

| INGREDIENTS | PERCENTAGE BY WEIGHT |
| --- | --- |
| Aloe Vera Extract | 45.20% |
| Sodium C-14-16 Olefin Sulfonate | 20.00% |
| Lecithin | 10.00% |
| Sodium Laureth Sulfate | 10.00% |
| Lauramide DEA | 5.00% |
| Cocamidopropyl Betaine | 3.00% |
| Allantoin | 2.00% |
| Chamomile Extract | 1.00% |
| Comfry Extract | 1.00% |
| Calendula | 1.00% |
| Tocopherol Acetate (Vitamin) | 1.00% |

TABLE 4-continued

Therapeutic Body Cleansing Lather

| INGREDIENTS | PERCENTAGE BY WEIGHT |
| --- | --- |
| Panathol | 0.20% |
| Sodium PCA | 0.20% |
| Tocopherol | 0.15% |
| Potassium Sorbate | 0.10% |
| Sodium Citrate | 0.10% |
| Lavender Essential Oil | 0.05% |

Many alterations may be made by those having ordinary skill in the art without departing from the spirit and scope of the invention. Therefore, it must be understood that the invention described above has been set forth in various examples as an illustration of the invention and should be taken as limiting the invention as defined in the following claims. The following claims must be construed to include not only what is literally claimed but all means for performing substantially the same function in substantially the same way to obtain substantially the same result.

I claim:

1. A mixture for treatment of irradiated skin, open sores, wounds and abrasions, said mixture comprising:
    a substantially anthraquinone-free cold processed fresh aloe vera extract, said aloe vera extract comprising from about 1 percent by weight per unit volume up to about 98 percent per unit volume; and
    allantion comprising from about 0.10 percent by weight per unit volume up to about 8 percent by weight per unit volume,
    whereby a combination is provided which synergistically increases the healing effect of each said mixture over that provided separately by its constituents.

2. The mixture of claim 1 further comprising a topical carrier.

3. The mixture of claim 1 further comprising a nondegradable extract of lavender essential oil from about 0.01 percent by weight per unit volume up to about 2 percent by weight per unit volume.

4. The mixture of claim 1 further comprising a cosmetic surfactant.

5. The mixture of claim 1 further comprising a cosmetic preservative.

6. The mixture of claim 1 wherein said aloe vera extract comprises from about 40 percent by weight per unit volume to about 95 percent by weight per unit volume.

7. The mixture of claim 1 wherein said allantoin comprises from about 1 percent by weight per unit volume to about 2 percent by weight per unit volume.

8. The mixture of claim 6 wherein said allantoin comprises from about 1 percent by weight per unit volume to about 2 percent by weight per unit volume.

9. The mixture of claim 1 wherein said fresh aloe vera has been processed from an aloe vera plant having an outer rind, sap and containing aloin, said outer rind, yellow sap and aloin being removed by a cold process to produce said substantially anthraquinone-free aloe vera extract.

10. The mixture of claim 9 wherein said anthraquinone-free aloe vera extract is ground, homogenized and processed into a stable aloe vera extract.

11. The mixture of claim 3 wherein said lavender essential oil comprises from about 0.03 percent by weight per unit volume up to about 0.09 percent by weight per unit volume.

12. The mixture of claim 1 wherein said aloe vera extract comprises about 77.7 percent by weight per unit volume and said allantoin comprises about 2 percent by weight per unit volume.

13. The mixture of claim 1 wherein said aloe vera extract comprises about 93.8 percent by weight per unit volume and said allantoin comprises about 2.0 percent by weight per unit volume.

14. The mixture of claim 1 wherein said aloe vera extract comprises about 45.2 percent by weight per unit volume and said allantoin comprises about 2.0 percent by weight per unit volume.

15. A mixture for damaged skin comprising:
    a substance for reducing inflammation of said skin; and
    a substance for simultaneously healing said skin, said substance for reducing inflammation coacting with said substance for healing said skin to accelerate action of said substance for healing.

16. The mixture of claim 15 further comprising a substance for calming nervous activity while simultaneously providing said substance for reducing inflammation and said substance for healing to holistically coact with each other to heal.

17. The mixture of claim 15 wherein said substance for reducing inflammation is cold processed anthraquinone-free aloe vera comprising not less than about 1 percent by weight per unit volume.

18. The mixture of claim 15 wherein said substance for healing comprises allantoin of not less than about 0.5 percent by weight per unit volume.

19. The mixture of claim 16 wherein said substance for calming comprises lavender essential oil of not less than about 0.01 percent by weight per unit volume.

20. The mixture of claim 1 wherein said allantoin is micronized to a size of 400 mesh or finer.

21. The mixture of claim 1 further comprising a nondegradable extract of lavender essential oil derived from *Lavendula officinalis*.

* * * * *